United States Patent [19]
Sohn et al.

[11] Patent Number: 5,792,646
[45] Date of Patent: Aug. 11, 1998

[54] **PROCESS FOR PREPARING *S. CEREVISIAE* CONTAINING ORGANICALLY BOUND GERMANIUM**

[75] Inventors: Tsang Uk Sohn; Won Jong Song, both of Seoul; Sang Chul Lee, Choongcheongbuk-do; Tae Kwang Oh, Daejeon-si, all of Rep. of Korea

[73] Assignee: Daijy Corporation, Seoul, Rep. of Korea

[21] Appl. No.: 654,039

[22] Filed: May 28, 1996

Related U.S. Application Data

[63] Continuation-in-part of Ser. No. 427,973, Apr. 20, 1995, abandoned, which is a continuation of Ser. No. 184,381, Jan. 21, 1994, abandoned.

[30] Foreign Application Priority Data

Nov. 29, 1993 [KR] Rep. of Korea ............. 93-25595

[51] Int. Cl.$^6$ .................................................. C12N 1/00
[52] U.S. Cl. .............. 435/243; 435/244; 435/255.1; 435/940; 435/41; 424/600; 426/62; 426/46; 426/44
[58] Field of Search ..................... 435/243, 255.1, 435/244, 940, 41; 424/600; 426/62, 46, 44

[56] References Cited

U.S. PATENT DOCUMENTS

| | | | |
|---|---|---|---|
| 3,912,817 | 10/1975 | Chandler et al. | 426/44 |
| 4,008,334 | 2/1977 | Hansen | 426/46 |
| 4,530,846 | 7/1985 | Nagodawithana et al. | 426/62 |

FOREIGN PATENT DOCUMENTS

| | | | |
|---|---|---|---|
| 3345211 | 6/1985 | Germany | C12N 1/16 |
| 53-127882 | 11/1978 | Japan | C12B 1/08 |
| 53-130483 | 11/1978 | Japan | C12C 11/08 |
| 54-002393 | 1/1979 | Japan | C12B 1/00 |

OTHER PUBLICATIONS

Yuanfang et al, Kexue Tongbao, 29(9):1261–4, (1984, Sep.).
Van Dyke et al, J. Ind. Micro., 4:299–306, (1989).
Wei, Shipin Kexue, 149:49–54, (1992).
Syldatk et al, Appl. Microbiol. Biotechnol., 27:152–158 (1987).
ATCC Catalogue of Yeasts, 18th Ed., Jong et al (Ed.), 1990, p. 166.

*Primary Examiner*—Irene Marx
*Attorney, Agent, or Firm*—Michael N. Meller

[57] ABSTRACT

A process for preparing strains of *Saccharomyces cerevisiae* containing at least 4,000 ppm of organically bound germanium based on the dry weight of the yeast is described.

2 Claims, 2 Drawing Sheets

PROCESS FOR PREPARING S. CEREVISIAE CONTAINING ORGANICALLY BOUND GERMANIUM

This is a continuation-in-part of U.S. Ser. No. 08/427,973 filed Apr. 20, 1995, which is a continuation of U.S. Ser. No. 08/184,381 filed Jan. 21, 1994 now abandoned.

FIELD OF THE INVENTION

This invention relates to Saccharomyces cerevisiae containing organically bound germanium and a process for preparing the same. More particularly, this invention relates to *Saccharomyces cerevisiae* containing at least 4,000 ppm of organically bound germanium which is bound to a constitution component in the strain cell by inducing mass inflow of germanium ion into the strain cell. This is accomplished by adding germanium during the cultivation of an adapted strain to facilitate the addition of germanium. This invention also involves a process for preparing the strain of *Saccharomyces cerevisiae* for germanium addition.

DESCRIPTION OF THE PRIOR ART

The term "organically bound germanium" used herein refers to a compound in which inorganic germanium ion is chemically bound to an organic compound such as an amino acid, organic acid or the like. It is known that the organically bound germanium is contained as a trace element in the living human body, and also in a very small amount (1–10 ppm) in most animals and plants. It is also known that the organically bound germanium is a principal component of mineral water such as miraculous spring water in the district of Lourdes in France, and it has an excellent effect in the treatment, alleviation or prevention of adult diseases such as cancer, hypertension, diabetes, heart disease, degenerative disease, rheumatoid arthritis and the like. Furthermore, it is known that the organically bound germanium has a potent immunity. In advanced countries including the United States, Japan and the like, studies on treatment of incurable diseases such as cancer, heart disease or the like by using organically bound germanium have been extensively carried out [Int.J.Radiat. Biol. Relat. Stud. Phys. Chem. Med.,42(6) ,653–9(1982); Anticancer Res.,5(5),479–483(1985)] Hitherto, the organically bound germanium has been obtained by an extraction method of natural substances such as ginseng or from the mineral water, or by a chemical synthesis inducing a reaction of organic acid with germanium dioxide by using a catalyst. However, the former method is performed at high cost while the latter method is lacking in safety. Thus, these conventional methods are not commercially available for foods or medicine.

Yeast has been used in brewing, baking and the like as a useful microorganism, and it has an important effect on human dietary life for several thousand years. The yeast itself is also a valuable nutrient source. Yeast has been highlighted as a protein source of the next generation, i.e., a single cell protein, characterized in that it contains low fat and high protein and evenly containing protein, vitamin, mineral and the like. Furthermore, yeast is a great source of the vitamin B group as a food unit, and it contains substantial amounts of enzymes which play a greater role in the metabolism in the living body. Thus, the yeast is useful as a health supplementary food.

U.S. Pat. No. 4,530,846 describes a method for the preparation of yeast containing organically bound selenium by adding the selenium to the culture medium and then cultivating. According to the process of the cited reference, the yeast is cultivated by continuously and incrementally adding selenium salt to a yeast in a growth medium, to obtain a selenium yeast. Japanese Patent Laid-Open Nos. (Sho)53–127, 882 and 53–130, 483 describe yeast containing germanium and a process for preparing thereof. In the latter processes, the yeast is cultivated in the culture medium with a simple addition of inorganic germanium. In general, the growth of the microorganism is inhibited by substantial amounts of inorganic additives including germanium. For this reason, the cultivation of yeast according to this prior art process is restricted and the yield of the yeast decreases, so that organically bound germanium cannot be obtained in high concentration.

SUMMARY OF THE INVENTION

The inventors have extensively studied a process for preparing organically bound germanium in substantial amounts. As a result, a process for preparing organically bound germanium in substantial amounts by utilizing an edible yeast has been accomplished.

In the present invention, a strain of *S. cerevisiae* is previously cultivated under the addition of low to high concentrations of germanium order in minimize the damage of yeast growth due to an abrupt concentration change of germanium by the supply of germanium, and then both germanium and glucose as a nutrient source are simultaneously supplied in the growth logarithmic phase of the strain to permit the flow of substantial amounts of germanium into the strain.

An object of the present invention is to provide a strain of *S. cerevisiae* containing substantial amounts of organically bound germanium and a process for preparing the same.

Another object of the present invention is to provide for the strain to remain actively growable *S. cerevisiae* even under the conditions of the addition of high concentrations of germanium.

The process of preparing a strain of *S. cerevisiae* containing organically bound germanium of at least 4,000 ppm according to the present invention involves; (a)initially, inoculating *S. cerevisiae* in a first culture medium consisting essentially of defatted soybean meal, yeast extract, glucose and water, wherein the medium contains $GeO_2$ of less than 1.0 g/l and selecting the live strains from this medium after cultivating, (b) inoculating the strains obtained from step (a) in a second culture medium wherein the medium contains higher amounts of $GeO_2$ than step (a) and selecting the live strain from the medium after cultivating, and optionally repeating the same procedure as in step (b) several times while the amounts of $GeO_2$ are increased in a stepwise manner, and (c) cultivating the strain obtained in step (b) in the culture medium, adding $GeO_2$ of 0.1 to 1.0 g/l thereto in the growth logarithmic phase of the strain to obtain a strain containing organically bound germanium of at least 4,000 ppm.

DETAILED DESCRIPTION OF THE INVENTION

In general, the growth of the microorganism is limited under the circumstance in which a high concentration of mineral exists. The inventors have extensively investigated among other various microorganisms, to determine the availability of a strain containing organically bound germanium. As a result, S. cerevisiae among the yeasts that contains various essential elements and makes it possible to utilize the intracellular components as an antitumor agent has been selected. The S. cerevisiae strains used herein are KCTC 1199, KCTC 1201, KCTC 1202, KCTC 1205, KCTC 1213 and KCTC 1215.

In order to determine the effect of the concentration of germanium ion in the culture medium as it affects the growth of the selected microorganisms, i.e., S. cerevisiae, the cultivation is carried out using various concentrations of $GeO_2$. As a result, it is observed that the mobility as well as the growth of the strain are lowered in the culture medium containing 0 g/l (100 ppm) or more of germanium.

Figure 1:
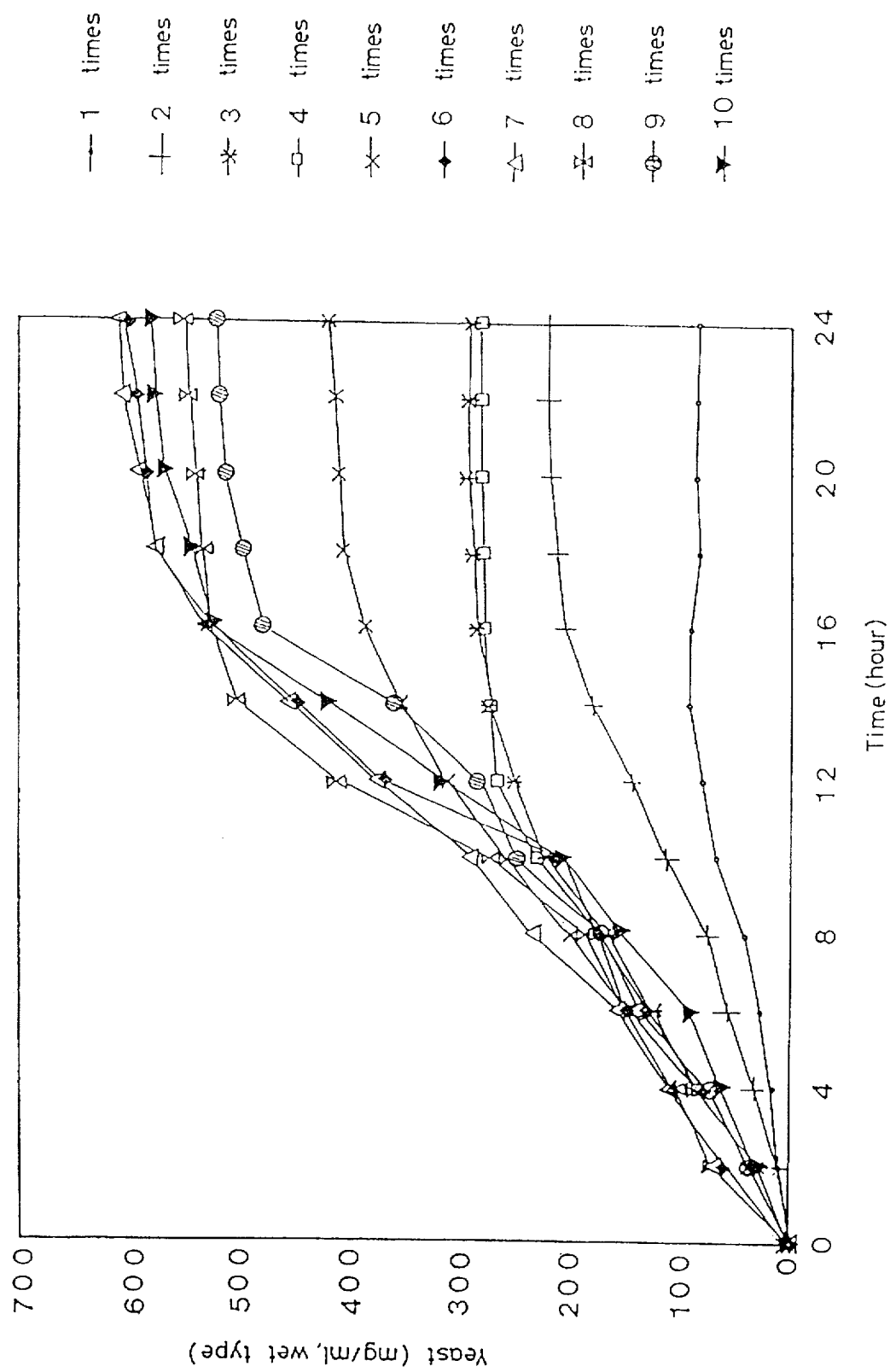
FIG. 1 is a graph showing the growth curve of the strain in the culture medium according to the present invention.

In order to overcome the above problem in the present invention, the strain, Saccharomyces cerevisiae, is previously cultivated by the procedure which comprises the replacement of the culture medium with a fresh culture medium containing increasing amounts of germanium. In other words, the strain is inoculated in one medium and cultivated, then followed by selecting the live strains therefrom. These selected strains are inoculated again in a fresh medium, cultivated and then the live strains are selected from the medium. The difference between each medium is in the amounts of Ge added thereto. The amount of Ge contained in each subsequent medium is more than the immediately preceding one. The strain throughout this procedure is the same strain as inoculated in the first medium but the live strains are selected from each medium. The resultant strain can grow actively even under the conditions of high concentrations of Ge. The number of replacements of culture medium may be optionally determined and is preferably 4 to 7 times. After the selection of the strain is completed, a growth curve is determined for the strain. The growth curve of the strain according to the present invention, is shown in FIG. 1. As can be seen in FIG. 1, the strains of the present invention represent their growth logarithmic phase at about 9 hours after inoculation. When the selected strains are cultivated and $GeO_2$ is added in its growth logarithmic phase, an inflow of Ge into the strain is increased unexpectedly. According to the present invention, an incorporation of Ge into the strain is increased at least 4 times more than the conventional method while the yield of the strain is not decreased. In order to incorporate a high concentration of organically bound germanium into the strain a culture medium containing 4.2 to 5.2 wt % of defatted soybean meal, 0.5 to 0.7 wt % of yeast extract and 6.5 to 7.5 wt % of glucose to the whole composition of the medium is used as a basic medium.

In an embodiment of the present invention, means of the above procedure, the above basic medium is added to the strain, further adding 0.1 to 1.0 g/l of germanium and 5 to 7 wt % of glucose as a nutrient source to the whole composition of the medium in the growth logarithmic phase of the adapted yeast. As a result, substantial amounts of organically bound germanium are incorporated into the adapted yeast strain.

In order to quantify the amount of germanium to be incorporated into the yeast, phenylfluorone is reacted with germanium to form a complex. This complex is then subjected to spectroscopy in order to determine its absorbance at 505 nm.

Figure 2:
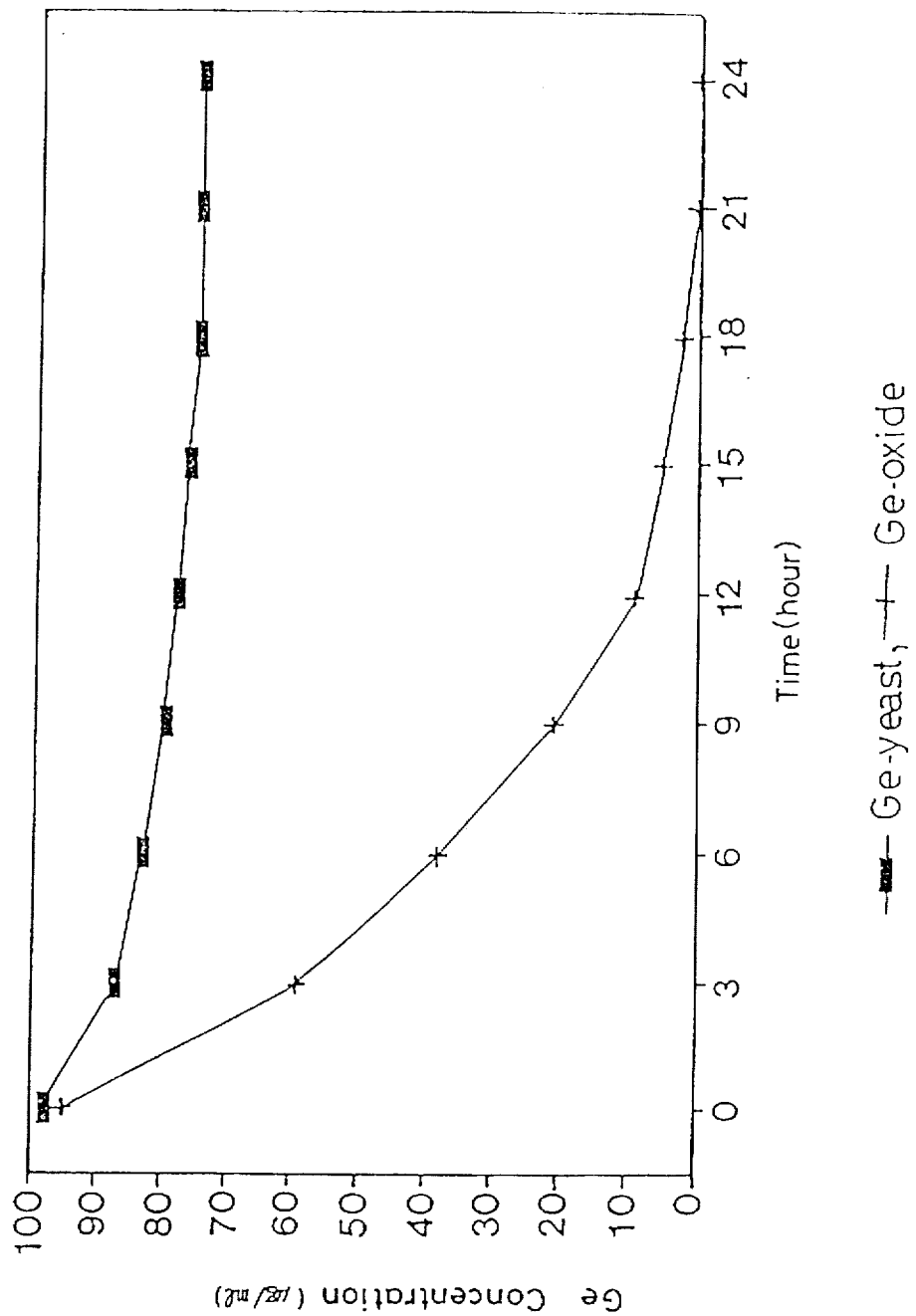
FIG. 2 is a graph showing the dialysis result of a strain solution according to the present invention and a solution of inorganic germanium.

Further, in order to ascertain whether the germanium incorporated into the yeast according to the present invention exists in the form of organically bound germanium, a solution of yeast according to the present invention and a solution of inorganic germanium are each dialyzed under the same conditions. The amount of germanium of each dialyzed solution is quantified. As shown in FIG. 2, the germanium in the yeast solution according to the present invention remains at a constant amount even over the lapse of time while the quantitative curve of inorganic germanium has rapidly dropped. More specifically, the inorganic germanium may easily pass the dialysis membrane since its molecular structure is very fine, and thus its quantitative curve rapidly drops. On the other hand, organically bound germanium of which germanium is associated with the macromolecular protein and the like in the yeast cell and is difficult to pass through the dialysis membrane. Thus, its quantitative curve does not greatly fall in spite of the lapse of time.

The experiments of the yeast containing organically bound germanium according to the present invention are carried out in accordance with the above analysis. As a result, at least 4,000 ppm (μg/g) of organically bound germanium has been quantified.

The following examples are given to illustrate this invention without limiting it in any way. The examples herein use a culture medium which comprises 4.2 to 5.2 wt. % of defatted soybean meal, 0.5 to 0.7 wt % of yeast extract and 6.5 to 7.5 wt % of glucose on the basis of the total weight of the culture medium wherein the remainder of the culture medium is water, and sterilized at about 121° C. for 15 minutes.

EXAMPLE 1

Determination of Optimum Medium Condition for Mass Production of Strain 1 v/v % of yeast was added to 100 ml of the culture medium containing each 1 wt % of meat extract, corn-steep liquid(CSL), malt extract, peptone, polypeptone, tryptone, soytone, yeast extract, defatted soybean meal and milk casein as a protein source, and each 1 wt % of glucose, lactose and sucrose as a carbohydrate source, and then cultivated with stirring at 170 rpm and at 28° C. for 24 hours. As a result, as shown in the following Table 1, the strains were produced with the most amount in both the carbohydrate source and the protein source.

TABLE 1

The Amount of production of Yeast according to the Carbohydrate and Protein Sources (mg/ml, wet type)

|  | Glucose | Lactose | Sucrose |
|---|---|---|---|
| meat extract | 32.3 | 24.6 | 27.1 |
| corn-steep liquid | 41.8 | 31.3 | 35.5 |
| malt extract | 21.7 | 18.5 | 22.1 |
| peptone | 27.6 | 24.2 | 29.0 |
| polypeptone | 24.7 | 20.2 | 23.1 |
| tryptone | 24.4 | 20.5 | 24.1 |
| soytone | 37.0 | 32.5 | 35.0 |
| yeast extract | 36.1 | 30.9 | 35.81 |
| defatted soybean meal | 72.6* | 39.7 | 41.1 |
| milk casein | 22.4 | 15.1 | 20.3 |
| control | 13.3 | 2.5 | 4.5 |

EXAMPLE 2

Determination of Ratio of Optimum Concentration of Nutrient 1 v/v % of yeast was inoculated in 100 ml of culture medium changed as shown in Table 2 below, which contains defatted soybean meal, glucose, and essential trace element which is necessary to produce the strain, all of which are excellent in the production of strain, and then cultivated with stirring at 170 rpm and at 28° C. for 24 hours. As a result, as shown in the following Table 2, the strains were produced with the most amount in the culture medium containing 1.0 wt % of glucose, 0.8 wt % of defatted soybean meal, 0.1 wt % of yeast extract and water. This medium was named as SY medium.

TABLE 2

Change of Amount of Production of Yeast According to the Ratio of Nutrient (%, mg/ml, wet type)

| Glu-cose | Defatted soybean meal | Yeast ex-tract | Product (Yeast) | Glu-cose | Defatted soybean meal | Yeast extract | Product (Yeast) |
|---|---|---|---|---|---|---|---|
| 1.0 | 0.2 | 0.1 | 54.3 | 1.0 | 0.5 | 0.5 | 67.6 |
| 1.0 | 0.2 | 0.2 | 47.5 | 1.0 | 0.6 | 0.1 | 75.1 |
| 1.0 | 0.2 | 0.3 | 51.0 | 1.0 | 0.6 | 0.2 | 81.0 |
| 1.0 | 0.4 | 0.1 | 67.1 | 1.0 | 0.6 | 0.3 | 69.8 |
| 1.0 | 0.4 | 0.2 | 61.3 | 1.0 | 0.6 | 0.4 | 67.0 |
| 1.0 | 0.4 | 0.3 | 71.4 | 1.0 | 0.8 | 0.1 | 87.0* |
| 1.0 | 0.4 | 0.4 | 68.4 | 1.0 | 0.8 | 0.2 | 81.3 |

EXAMPLE 3

Determination of Degree of Concentration of Culture Medium for Mass Production of Strain In order to obtain a culture medium which is able to maximize the yield of production of the strain and to increase the content of germanium in the strain, the yeast was inoculated in the above culture medium, in which the concentration of SY medium determined in Example 2 was changed as those shown in the following Table 3, and then cultivated with stirring at 170 rpm and at 28° C. for 24 hours. As a result, as shown in Table 3, the best medium having a high yield of production of the strain was a 6 times-concentrated medium.

This medium contains 4.8 wt % of defatted soybean meal, 0.6 wt % of yeast extract, 6.0 wt % of glucose and water, and it is named as SY-6 medium. The curve of its growth is shown in FIG. 1.

and cultivated at 30° C. for 48 hours. The live strains were recovered from the medium.

(2) $GeO_2$ in an amount of 1.2 g/l was added to the culture medium, the strain which was selected in (1) was inoculated and cultivated at 30° C. for 48 hours. The live strains were recovered from the medium.

(3) $GeO_2$ in an amount of 2.8 g/l was added to the culture medium, the strain which was selected in (2) inoculated and cultivated at 30° C. for 48 hours. The live strains were recovered from the medium.

(4) $GeO_2$ in an amount of 3.8 g/l was added to the culture medium, the strain which was selected in (3) was inoculated and cultivated at 30° C. for 48 hours. The live strains were recovered from the medium. A growth logarithmic phase was determined on the obtained strain.

*Saccharomyces cerevisiae* KCTC 1199, KCTC 1201, KCTC 1202, KCTC 1205, KCTC 1213, and KCTC 1215 were used as a strain.

EXAMPLE 5

The procedures were the same as shown for example 4, except that 1.0 g/l of $GeO_2$ was added to the culture medium in (1), 2.0 g/l to the culture medium in (2), 3.0 g/l to the culture medium in (3), 4.0 g/l to the culture medium in (4), and additionally the strain was selected from the medium in (4) and then inoculated into the culture medium containing $GeO_2$ of 5 g/l to obtain the final strain. A growth logarithmic phase was determined on the obtained strain.

*Saccharomyces cerevisiae* KCTC 1199, KCTC 1201, KCTC 1202, KCTC 1205, KCTC 1213, and KCTC 1215 were used as a strain.

Comparative Example 1

*Saccharomyces cerevisiae* was inoculated and cultivated in the culture medium of which 0.6 to 3.8g/l $GeO_2$ was added in portions at 30° C. for 48 hours. The live strains were selected from the medium.

*Saccharomyces cerevisiae* KCTC 1199, KCTC 1201, KCTC 1202, KCTC 1205, KCTC 1213 and KCTC 1215 were used as a strain.

EXAMPLE 6

Each strain of example 4 was inoculated in a fermenter containing 3 liters of the culture medium at a pH of 5.5 and

TABLE 3

Degree of Concentration of Culture Medium and Amount of Production of Yeast according to Lapse of Time (mg/ml, wet type)

|  | 1 time | 2 times | 3 times | 4 times | 5 times | 6 times | 7 times | 8 times | 9 times | 10 times |
|---|---|---|---|---|---|---|---|---|---|---|
| 2 Hr | 9.9 | 10.8 | 28.5 | 27.3 | 28.1 | 67.8 | 58.2 | 69.1 | 36.5 | 30.1 |
| 4 Hr | 15.7 | 32.9 | 84.8 | 85.1 | 85.2 | 109.3 | 109.4 | 103.9 | 74.2 | 61.4 |
| 6 Hr | 27.7 | 57.8 | 124.8 | 129.5 | 145.6 | 146.2 | 156.1 | 148.4 | 153.7 | 92.2 |
| 8 Hr | 42.4 | 76.9 | 166.1 | 172.3 | 202.4 | 172.8 | 233.6 | 186.9 | 171.2 | 152.2 |
| 10 Hr | 68.3 | 113.9 | 221.6 | 230.0 | 260.0 | 205.1 | 289.3 | 272.0 | 248.8 | 204.8 |
| 12 Hr | 82.1 | 143.4 | 253.1 | 268.3 | 313.3 | 372.0 | 376.8 | 411.8 | 286.1 | 316.3 |
| 14 Hr | 93.9 | 180.5 | 273.5 | 275.4 | 354.8 | 447.2 | 453.6 | 500.6 | 360.5 | 418.2 |
| 16 Hr | 93.2 | 204.8 | 286.4 | 279.5 | 386.6 | 525.0 | 532.8 | 526.9 | 476.5 | 525.4 |
| 18 Hr | 85.9 | 212.4 | 288.6 | 281.1 | 405.4 | 578.2 | 579.2 | 536.5 | 496.2 | 545.0 |
| 20 Hr | 88.4 | 218.3 | 294.0 | 282.5 | 410.2 | 587.4 | 592.3 | 541.8 | 512.5 | 570.4 |
| 22 Hr | 87.0 | 221.3 | 295.4 | 282.2 | 413.5 | 595.2 | 608.7 | 548.2 | 518.4 | 578.5 |
| 24 Hr | 85.7 | 220.1 | 293.4 | 282.6 | 418.6 | 608.1 | 612.4 | 550.5 | 521.5 | 582.4 |

EXAMPLE 4

Selection (Recovery) of the Strain (1) $GeO_2$ in an amount of 0.6 g/l was added to the culture medium. *Saccharomyces cerevisiae* was inoculated thereto cultivated at 30° C. while stirring at 400 rpm and aerated in amounts of 1 v/vm for 48 hours. Meanwhile, 0.1 g/l of $GeO_2$ and 5 wt % of glucose on the basis of the weight of the culture medium were added to the medium in 9 to 15 hours after inoculation. The strain was cultivated until it reached the growth stationary phase.

The cultivated solution was centrifuged and the precipitate thus obtained was washed with physiological saline solution and distilled water each three times.

The strain products were completely crushed and then the concentration of germanium was determined at 505 nm by UV-VIS spectrophotometry, which was the same method as Example 8.

The results are shown in Table 4.

Comparative Example 2

The procedure was carried out in the same way as example 6, except for using the strain of comparative example 1.

The cultivated solution was centrifuged and the precipitate thus obtained was washed with physiological saline solution and distilled water each three times.

The strain products were completely crushed and then the concentration of germanium was determined at 505 nm by UV-VIS spectrophotometry which was the same method as Example 8.

The results are shown in table 4.

TABLE 4

| Organisms *1 | | Yield *2 (g/L) | Ge content *3 [μg/g(ppm)] |
|---|---|---|---|
| Example 4 | KCTC 1199 | 36.4 | 4,680 |
| | KCTC 1201 | 32.1 | 4,490 |
| | KCTC 1202 | 32.9 | 4,370 |
| | KCTC 1205 | 30.1 | 4,380 |
| | KCTC 1213 | 25.5 | 4,390 |
| | KCTC 1215 | 25.7 | 4,210 |
| Comparative | KCTC 1199 | 25.1 | 1,980 |
| Example 2 | KCTC 1201 | 22.5 | 1,820 |
| | KCTC 1202 | 22.9 | 1,940 |
| | KCTC 1205 | 22.1 | 1,900 |
| | KCTC 1213 | 21.3 | 1,910 |
| | KCTC 1215 | 21.3 | 1,800 |

*1 All strains are *Saccharomyces cerevisiae*.
*2 Yield: dried strains product g/l medium.
*3 Ge content μg/g the dried strain.

EXAMPLE 7

Each strain of example 5 was inoculated in the fermenter containing the 3 liters of the culture medium at a pH of 5.5 and cultivated at 30° C., stirred at 400 rpm and aerated in amounts of 1 v/v/m for 48 hours. Meanwhile, 1.0 g/l of $GeO_2$ and 7 wt % of glucose on the basis of the weight of the culture medium were added to the medium at the time of inoculation, 9 hours and 36 hours after inoculation, respectively.

The strain was cultivated until it reached the growth stationary phase.

The cultivated solution was centrifuged and the precipitate thus obtained was washed with physiological saline solution and distilled water each three times.

The strain products were completely crushed and then the concentration of germanium was determined at 505 nm by UV-VIS spectrophotometry which was the same method as Example 8.

The results are shown in table 5.

Comparative Example 3

Each strain of comparative example 1 was cultivated by the same method as example 7. The cultivated solutions were centrifuged and the precipitates thus obtained were washed with physiological saline solution and distilled water each three times.

The strain products were completely crushed and then the concentration of germanium was determined at 505 nm by UV-VIS spectrophotometry which was the same method as Example 8.

The results are shown in table 5.

TABLE 5

| | | Addition Time after inoculation(hour) | | | | | |
|---|---|---|---|---|---|---|---|
| | | 0 | | 9 | | 36 | |
| Organisms*1 | | Yield*2 | Ge content*3 [μg/g(ppm)] | Yield | Ge content [μg/g(ppm)] | Yield | Ge content [μg/g(ppm)] |
| Example 7 | KCTC 1199 | 20.9 | 2,420 | 28.1 | 4,550 | 30.3 | 2,780 |
| | KCTC 1201 | 14.7 | 2,120 | 22.4 | 4,340 | 27.4 | 2,240 |
| | KCTC 1202 | 15.6 | 2,130 | 24.5 | 4,210 | 27.5 | 2,350 |
| | KCTC 1205 | 17.3 | 2,410 | 20.3 | 4,250 | 28.4 | 2,460 |
| | KCTC 1213 | 16.4 | 2,170 | 19.4 | 4,330 | 28.5 | 2,320 |
| | KCTC 1215 | 13.1 | 2,030 | 19.1 | 4,180 | 27.2 | 2,110 |
| Comparative | KCTC 1199 | 13.4 | 1,360 | 21.6 | 1,950 | 30.2 | 1,450 |
| Example | KCTC 1201 | 11.7 | 1,170 | 19.4 | 1,770 | 28.9 | 1,360 |
| 3 | KCTC 1202 | 9.6 | 1,330 | 20.1 | 1,920 | 28.4 | 1,430 |
| | KCTC 1205 | 10.5 | 1,220 | 19.0 | 1,840 | 28.7 | 1,420 |
| | KCTC 1213 | 9.3 | 1,270 | 18.1 | 1,840 | 27.1 | 1,410 |
| | KCTC 1215 | 9.2 | 1,140 | 18.2 | 1,750 | 27.1 | 1,430 |

*1 All strains are *Saccharomyces cerevisiae*.
*2 Yield: dried strains product g/l medium.
*3 Ge content μg/g of the dried strain.

EXAMPLE 8

Standardization for Quantification of Germanium

A solution of germanium(Aldrich, 10,000 µg/l) was diluted into the solution of 0 to 10,000 µg/l. 1 ml of each solution was reacted with 0.04% solution of phenylfluorone dissolved in 100 ml of ethanol containing 0.43 ml of 6N HCl to form a complex. To this solution was added $2 \times 10^{-3}\%$ of Arabic gum as a stabilizer, followed by addition of $2 \times 10^{-4}\%$ of ammonium bromide to amplify the absorbance, and then allowed to stand for 20 minutes. A mixture solvent of chloroform and ethanol(3:2) was added thereto. This solution was vigorously agitated for 5 minutes, and the separated organic solvent layer was then transferred into a quartz cell. The absorbance was determined at 505 nm. The change of absorbance according to the concentration of germanium is shown in the following Table 6. The result thus obtained was used as a standard quantitative curve.

TABLE 6

Change of Absorbance according to the Concentration of Germanium

| Concentration (µg/l) | 0 | 100 | 200 | 400 | 600 | 800 | 1000 |
|---|---|---|---|---|---|---|---|
| Absorbance (505 nm) | 0.0 | 0.057 | 0.129 | 0.224 | 0.302 | 0.427 | 0.588 |

EXAMPLE 9

Confirmation on Conversion of Inorganic Germanium Incorporated into Organically Bound Germanium.

The strain containing organically bound germanium obtained from Example 6 was completely crushed, and the initially contained amount of germanium was quantified in accordance with the method of Example 8. 20 ml of solution of the crushed strain was taken, and put in a dialysis tube. Meanwhile, the initial amount of germanium in 0.01M germanium oxide solution was quantified, and 20 ml of this solution was put in a dialysis tube. The above two dialysis tubes were dialyzed in a 1 liter flask containing 500 ml of dialysis solution, respectively. In this connection, distilled water was used as a dialysis solvent, and the dialysis solvent was changed at intervals of 6 hours. 1 ml of sample from each dialysis tube was taken every three hours, and then the amount of germanium was quantified in accordance with the method of Example 8.

The results thus obtained are shown in the following Table 7 and FIG. 2, respectively. From the above results, it can be seen that the amount of reduction in germanium content of the strain solution is less than the one in inorganic germanium, i.e., germanium oxide. That is, germanium in the strain cell was bound to a macromolecular organic substance which cannot pass the dialysis membrane.

TABLE 7

Change of Concentration of Germanium by Dialysis (µg/l)

| Time (hr) | 0 | 3 | 6 | 9 | 12 | 15 | 18 | 21 | 24 |
|---|---|---|---|---|---|---|---|---|---|
| Strain extract | 98 | 87 | 83 | 80 | 78 | 77 | 75 | 75 | 75 |
| Germanium oxide | 95 | 59 | 38 | 21 | 9 | 5 | 2 | 0 | 0 |

What claimed is:

1. A process for preparing strains of *Saccharomyces cerevisiae* containing organically bound germanium of at least 4,000 ppm on the basis of a dry weight of the yeast which comprises:

a) inoculating *S. cerevisiae* to a first culture medium consisting essentially of 4.2 to 5.2 wt % of defatted soybean meal, 0.5 to 0.7 wt % of yeast extract and 6.5 to 7.5 wt % of glucose on the basis of the total weight of the culture medium wherein the remainder of the culture medium is water and 1.2 to 2.0 g/l of $GeO_2$, cultivating and then collecting live strains from the medium;

b) inoculating the strains obtained from step (a) to a second culture medium consisting essentially of 4.2 to 5.2 wt % of defatted soybean meal, 0.5 to 0.7 wt % of yeast extract and 6.5 to 7.5% of glucose on the basis of the total weight of the culture medium wherein the remainder of the culture medium is water and 1.2 to 2.0 g/l of $GeO_2$, cultivating and then collecting live strains from the medium;

c) inoculating the strains obtained from step (b) to a third culture medium consisting essentially of 4.2 to 5.2 wt % of defatted soybean meal, 0.5 to 0.7 wt % of yeast extract and 6.5 to 7.5 wt % of glucose on the basis of the total weight of the culture medium wherein the remainder of the culture medium is water and 2.8 to 3.0 g/l of $GeO_2$, cultivating and then collecting live strains from the medium; and d) cultivating the strains obtained from step (c) in the culture medium consisting essentially of 4.2 to 5.2 wt % of defatted soybean meal, 0.5 to 0.7 wt % of yeast extract and 6.5 to 7.5 wt % of glucose on the basis of the total weight of the culture medium wherein the remainder of the culture medium is water, followed by adding 0.1 to 1.0 g/l of $GeO_2$, and 5 to 7 wt % of glucose on the basis of the weight of the medium to the culture medium in the growth logarithmic phase of said strains and cultivating to obtain said strains containing organically bound germanium wherein the initial strains of *S. cerevisiae* are selected from the group consisting of KCTC 1199, 1201, 1202, 1205, 1213 and 1215.

2. A process according to claim 1, wherein the strains of step (b) are subjected to the treatment of step (b) one or more additional times.

* * * * *